(12) United States Patent
Geng et al.

(10) Patent No.: US 8,383,708 B2
(45) Date of Patent: Feb. 26, 2013

(54) EPOXIDIZED SOYATE DIESTERS AND METHODS OF USING SAME

(75) Inventors: Kebin Geng, Rocky River, OH (US); Roger W. Avakian, Aurora, OH (US); Louis Dupont, St. Remi de Napierville (CA); Stephen D. Horton, Avon Lake, OH (US)

(73) Assignee: Polyone Coporation, Avon Lake, OH (US)

( * ) Notice: Subject to any disclaimer, the term of this patent is extended or adjusted under 35 U.S.C. 154(b) by 154 days.

(21) Appl. No.: 12/867,211

(22) PCT Filed: Feb. 4, 2009

(86) PCT No.: PCT/US2009/033043
§ 371 (c)(1),
(2), (4) Date: Aug. 11, 2010

(87) PCT Pub. No.: WO2009/102592
PCT Pub. Date: Aug. 20, 2009

(65) Prior Publication Data
US 2010/0324185 A1    Dec. 23, 2010

Related U.S. Application Data

(60) Provisional application No. 61/027,896, filed on Feb. 12, 2008.

(51) Int. Cl.
*C08K 5/15*    (2006.01)

(52) U.S. Cl. ........ 524/114; 502/340; 502/342; 502/350; 549/514; 549/539

(58) Field of Classification Search .................. 524/114; 549/514, 539; 502/340, 342, 350
See application file for complete search history.

(56) References Cited

U.S. PATENT DOCUMENTS

| | | | |
|---|---|---|---|
| 2,978,463 | A | 4/1961 | Kuester et al. |
| 3,070,608 | A | 12/1962 | Kuester et al. |
| 4,581,413 | A | 4/1986 | Kim |
| 4,693,800 | A | 9/1987 | Edwards et al. |
| 4,939,212 | A | 7/1990 | Mikofalvy et al. |
| 5,290,890 | A | 3/1994 | Kim et al. |
| 5,324,846 | A | 6/1994 | Hirshmann et al. |
| 5,643,501 | A | 7/1997 | Buan et al. |
| 5,728,779 | A | 3/1998 | van de Werff et al. |
| 6,573,354 | B1 | 6/2003 | Petrovic et al. |
| 6,797,753 | B2 | 9/2004 | Benecke et al. |
| 7,071,343 | B2 | 7/2006 | Daute et al. |
| 7,326,763 | B2 | 2/2008 | Kamps et al. |
| 2010/0292492 | A1 | 11/2010 | Geng et al. |

FOREIGN PATENT DOCUMENTS

EP    0 295 534    12/1988

*Primary Examiner* — Peter D Mulcahy
(74) *Attorney, Agent, or Firm* — John H. Hornickel

(57) ABSTRACT

An unhindered polyol is used to react with an epoxidized soyate to make epoxidized soyate diester in the presence of a catalyst. The unhindered polyol can be 1,3-propanediol or any polyol having four or more carbon atoms with no two adjacent carbon atoms having hydroxyl functionality. Preferably, a combination of catalysts is used to promote the transesterification reaction of the epoxidized soyate with the unhindered polyol to yield a high percentage of epoxidized soyate diester with epoxy functionality retained. The primary catalyst is a metallic hydroxide, and the secondary catalyst is a titanate. Bioderived epoxidized soyate diester plasticizers useful for thermoplastics and thermosets result.

18 Claims, No Drawings

EPOXIDIZED SOYATE DIESTERS AND METHODS OF USING SAME

CLAIM OF PRIORITY

This application claims priority from U.S. Provisional Patent Application Ser. No. 61/027,896 and filed on Feb. 12, 2008, which is incorporated by reference.

FIELD OF THE INVENTION

This invention relates to epoxidized soyate diesters and their use as plasticizers for rigid thermoplastic compounds.

BACKGROUND OF THE INVENTION

Plasticizers from petroleum feedstocks and other synthetic sources have been dominant in industry since the mid-Twentieth Century following the polymerization of vinyl chloride and a need to make that polyvinyl chloride flexible. Phthalate plasticizers have been most prevalent.

Plasticizers from biological, renewable sources have been explored in recent years because of concerns about availability of petroleum feedstocks, cost, and asserted health concerns.

U.S. Pat. No. 6,797,753 (Benecke et al.) teaches the manufacture of a number of epoxidized diesters from fatty acids, including epoxidized propylene glycol disoyate. The method used by Benecke et al. begins with an esterification reaction followed by an epoxidation. This is a complicated reaction route, because of the use of strong oxidants during epoxidation and the generation of waste streams following epoxidation that require environmental attention.

SUMMARY OF THE INVENTION

What the art needs is epoxidized soyate diesters easily made from naturally occurring, renewable feedstocks in a manner which retains the highly reactive epoxy moieties of the resulting diester.

The method of manufacture by Benecke et al. involving epoxidation after esterification has not been found to be suitable for small scale customized synthesis of plasticizers, which needs to avoid the establishment of a large scale reaction facility equipped to deal with strong oxidants as reagents and an environmentally complicated waste streams. One of the diesters identified by Benecke et al. is epoxidized propylene glycol disoyate, an epoxidized soyate diester also known as epoxidized propanediol disoyate.

But Benecke et al. do not identify which isomer of propylene glycol they used. Unfortunately, it is quite difficult to prepare epoxidized 1,2 propanediol disoyate where the reaction employed is transesterification of an epoxidized soyate. As stated above, Benecke et al. teach epoxidation after esterification in order to achieve their epoxidized propylene glycol disoyate.

The present invention solves the problem in the art by starting with an epoxidized soyate and promoting a transesterification reaction via a polyol in which no two hydroxyl groups are bonded to adjacent carbon atoms and the use of a combination of catalysts which results in an excellent retention of intact epoxy groups on the resulting epoxidized soyate diester.

Thus, the present invention solves the problem in the art by recognizing that polyols must have at least one carbon atom separating hydroxyl-containing carbon atoms. Therefore, the only propanediol suitable for the present invention is 1,3 propanediol. Thereafter, any and all polyols having at least four carbon atoms and no two adjacent carbon atoms both having hydroxyl functionality are suitable for use in the present invention.

The soyate diesters which result from reaction with these acceptable polyols are not subject to steric hindrance and other complications of having two long-chain fatty acid esters grafted to a polyol at adjoining carbon atoms via hydroxyl groups. Therefore, for purposes of this invention, these acceptable polyols are called "unhindered polyols."

Beginning with a commercially available epoxidized soyate, made at a large facility dedicated to handle the oxidants and waste streams mentioned above, and using unhindered polyols, one can then proceed to a transesterification reaction at a much less complicated facility, perhaps even one associated with chemical compounds that are made with the resulting epoxidized soyate diester.

One aspect of the present invention is a method of making an epoxidized soyate diester, comprising the step of mixing under heat and agitation epoxidized soyate, an unhindered polyol, and a catalyst to make an epoxidized soyate diester.

Preferably, the catalyst employed is a catalyst system, comprising: (a) a primary catalyst comprising a metallic hydroxide and (b) a secondary catalyst comprising a titanate.

Optionally but preferably, the primary catalyst also comprises a monool as a solvent/reactant for the metallic hydroxide if the latter is in solid form.

Another aspect of the present invention is any of the epoxidized soyate diesters resulting from the method described above, including without limitation, epoxidized 1,3-propanediol disoyate, epoxidized 1,4-butanediol disoyate, and epoxidized 1,6-hexanediol disoyate.

Surprisingly, the efficiency of the reaction using unhindered 1,3-propanediol can be as high as 96% and the yield of desired diester can be as high as 80%.

It is an advantage of the present invention that the use of unhindered polyols, as defined above, allows for efficiency of transesterification of epoxidized soyates in which the long soyate chains separated by at least one carbon atom in the polyol chain do not encumber each other or the kinetics of the transesterification reaction.

It is an advantage of the present invention that the combination of catalysts, with the metallic hydroxide serving as the primary catalyst and the titanate serving as the secondary catalyst results, unexpectedly, in a high-yielding epoxidized soyate diester with the epoxy groups of the plasticizer molecule remain intact. The epoxy groups survive the efficient transesterification reaction, which is unexpected when compared to the disclosure of Benecke et al. which requires epoxidation to follow esterification.

Other features and advantages of the invention will be explained below.

EMBODIMENTS OF THE INVENTION

Reactants

Epoxidized Soyates

Any bioderived epoxidized soyate is a suitable candidate for use in the present invention. It is understood that "soyate" is a carboxylate moiety which refers to any naturally occurring or subsequently refined mixture of fatty acids and their esters, where the fatty acids include palmitic acid, stearic acid, oleic acid, linoleic acid, linolenic acid, and the like. Epoxidation of the unsaturated fatty acid esters, even in the form of a methyl ester such as methyl soyate, typically generates an epoxy group, also called a glycidyl group or oxirane ring, replacing a double bond in the fatty acid backbone.

Often, the bioderived feedstock to making bioderived epoxidized soyates is epoxidized soybean oil (ESO), a known commercial commodity from biological origin. Several of its possible monoesters are also commercially available. Non-limiting examples of epoxidized soyate monoesters include epoxidized methyl soyate, epoxidized ethyl soyate, epoxidized butyl soyate, epoxidized octyl soyate, and combinations thereof. Of these, epoxidized methyl soyate (CAS No. 68082-35-9) is preferred.

The epoxidized soyate monoester can be commercially purchased or made from the reaction of epoxidized soybean oil with an alcohol such as methanol in the presence of a metallic hydroxide as a catalyst at a temperature of between 23° C.-45° C. and a 1 atmosphere (ambient) pressure and 50% relative humidity for approximately 36 hours using a round bottom flask reaction vessel. Another description of the synthesis of epoxidized methyl soyate can be found in Holser, "Transesterification of epoxidized soybean oil to prepare epoxy methyl esters" *Industrial Crops and Products* 27 (2008) 130-132 and Miyagowa et al., "Thermo-Physical and Impact Properties of Epoxy Containing Epoxidized Linseed Oil, 1 Anhydride-Cured Epoxy" *Macromol. Mater. Eng.* 2004, 289, 629-635, both of which are incorporated by reference.

A commercial source of epoxidized soyates is the Vikoflex® 7010 brand epoxidized methyl soyate from Arkema of Philadelphia, Pa.

Epoxidized soyate, to be useful in the present invention, should have from about 0.5 to about 4, and preferably from about 1 to about 2 epoxy groups on the side chain(s) of the molecule. This amount is the starting point and the ideal completion point of epoxy content in the resulting epoxidized soyate diester. Therefore, whether purchasing from commercial sources or making a precursor, the epoxy groups are important to the completion of a successful reaction in the presence of the catalysts.

Unhindered Polyol

Any unhindered alkyl polyol, preferably a bioderived polyol, is a suitable candidate for use in the present invention. Non-limiting examples of polyols are 1,3-propanediol, 2-methyl-1,3-propanediol, 2,2'-dimethyl-1,3-propanediol, 1,3-butanediol, 1,4-butanediol, 2-methyl-1,4-butanediol, 1,5-pentanediol, 2-methyl-2,4-pentanediol, 3-methyl-1,5-pentanediol, 1,3-hexanediol, 1-4-hexanediol, 1,5-hexanediol, 1,6-hexanediol, 2,2'-dihydroxypropyl ether, diethylene glycol, dipropylene glycol, triethylene glycol, and combinations thereof. Diols are preferred because they generally exhibit better permanence, better plasticizing ability, and less volatility with polyvinyl halides than other polyols. However, triols, tetraols, etc. are also candidates for use in the present invention so long as no two hydroxyl functionalities are on adjoining carbon atoms. Of preferred diols, 1,3-propanediol is most preferred, because of a balance of cost vs. performance, especially yield of diester in the transesterification reaction.

The density of epoxy groups per molecule of the resulting epoxidized soyate diester can also be a factor in the selection of polyol. The reaction of a polyol with two of the same or different epoxidized soyates creates an A-B-A/C structure, where A/C denotes that the polyol B reacts with either another A soyate or a different C soyate. All other things being constant, the length of the carbon chain of the polyol will affect the density of the epoxy groups per molecule.

To demonstrate the effectiveness of the method of the present invention, 1,3 propanediol (CAS No. 504-63-2), 1,4-butanediol, and 1,6-hexanediol were used.

A commercial source of 1,3-propanediol is Fluka brand propanediol from Aldrich Chemicals. Another source is Shell Chemicals. A commercial source of 1,4-butanediol is Lyondell Chemicals. A commercial source of 1,6-hexanediol is BASF.

Catalysts

Any conventional catalyst(s) used in transesterification is a candidate for use in the present invention. An extensive list of transesterification catalysts is disclosed in U.S. Pat. No. 7,326,763 (Kamps et al.) reciting, among others, alkali metal hydroxides (e.g., lithium hydroxide, sodium hydroxide, potassium hydroxide, and mixtures thereof); alkaline earth metal hydroxides (e.g., calcium hydroxide, barium hydroxide, and mixtures thereof); alkali metal salts of carboxylic acids (e.g., lithium acetate, sodium benzoate, and dipotassium dodecanedioate); alkaline earth metal salts of carboxylic acids (e.g., calcium benzoate, calcium adipate, and barium acetate); salts of a polycarboxylic acid (e.g., tetrasodium ethylenediamine tetracarboxylate and disodium magnesium ethylenediamine tetracarboxylate); and salts of non-volatile acids (e.g., alkaline earth metal salts of phosphates, alkali metal salts of phosphates, alkaline earth metal salts of phosphates, alkali metal salts of sulfates, alkaline earth metal salts of sulfates, alkali metal salts of metal oxo acids, and alkaline earth metal salts of metal oxo acids).

Other non-limiting examples of catalysts include tin, germanium, zirconium compounds, alkaline and alkaline earth metal oxides (e.g. magnesium oxide and especially nano MgO, hydrous metal oxides (e.g. $TiO_2$), titanium, zirconium, hafnium alkoxides and other oxygen containing alkoxides (e.g. metaloxyls such as titanyls), and combinations thereof. It is also possible that these reactions can be accelerated by ultrasound and microwave excitation, and or by carrying out the reaction in supercritical solvents, such as supercritical $CO_2$. Acceleration of the reaction by depositing or creating these materials in a nano form is also contemplated to improve reaction rate and possibly selectivity.

Preferably, however, it has been found by some of the inventors of this invention that a combination of a primary catalyst and a secondary catalyst works unexpectedly well.

Primary Catalyst

Any metallic hydroxide is a suitable candidate for use as a primary catalyst in the present invention. Non-limiting examples of metallic hydroxides include alkali and alkaline earth metal hydroxides. Of those, sodium, potassium, calcium, and magnesium hydroxide are most common, and potassium hydroxide is more preferred as the primary catalyst for this reaction because of its higher solubility and catalytic activity than other metallic hydroxides.

Potassium hydroxide is a commodity chemical available from any number of sources, include Sigma-Aldrich. If obtained in the form of flakes, methanol can be used to dissolve the flakes prior to introduction into the reaction vessel. Of all metallic hydroxides, potassium hydroxide has the highest solubility into methanol.

Dilution of KOH flakes into methanol can generate a solution ranging from about 1 to about 30, and preferably from about 10 to about 15 percent KOH in methanol.

Secondary Catalyst

Any titanium catalyst is a candidate as the secondary catalyst in the present invention. Non-limiting examples of titanium-based catalysts include such as 2-ethylhexyl titanate, tetraisopropyl titanate, tetrabutyl titanate, tetrakis-2-ethylhexyl titanate, and combinations thereof. Of these candidates, tetrakis-2-ethylhexyl titanate (CAS No. 1070-10-6) is preferred because of its balance of catalytic activity and robustness against the effects of hydrolysis in the presence of atmospheric moisture which leads to inactivity.

Experiments thus far have shown that while more simply structured titanates such as tetraisopropyl titanate can catalyze the reaction to generate minor diester yields, with more work to be done toward optimization of reaction, the more complicated structured titanates such as tetrakis-2-ethylhexyl titanate are already capable of producing commercially practical yields. Therefore, one of ordinary skill in the art without undue experimentation can select from various titanates, or combinations of them, for use as the secondary catalyst in the present invention.

Table 1 shows acceptable, desirable, and preferred ranges of the reactants and catalysts and optional solvent, expressed in moles.

TABLE 1

| Ingredient | Ingredients (Moles) | | |
| --- | --- | --- | --- |
| | Acceptable | Desirable | Preferred |
| Epoxidized soyate | 1.0 | 1.0 | 1.0 |
| Unhindered Polyol | 0.2-0.5 | 0.35-0.45 | 0.40-0.45 |
| Metallic hydroxide | 0.01-0.02 | 0.01-0.02 | 0.01-0.02 |
| Titanate | 0.007-0.015 | 0.007-0.015 | 0.007-0.015 |
| Optional alcohol solvent | 0-0.22 | 0-0.22 | 0-0.22 |

Processing

The preparation of the epoxidized soyate diesters in the presence of the catalysts occurs in a magnetically stirred reaction vessel heated to a temperature from about 60° C. to about 80° C., and preferably from about 65° C. to about 75° C. for about 18-22 hours while undergoing vigorous mixing using the magnetic stirrer. Nitrogen (blanketing) protection is also required because of the reactivity of the titanate catalyst.

The order of addition of the ingredients begins with the two reactants and the primary catalyst, stirring for approximately 30 minutes under a nitrogen atmosphere, followed by the addition of the secondary catalyst and further stirring under a nitrogen atmosphere for several hours.

A liquid is the reaction product, as one would hope for a epoxidized soyate diester to be useful as a plasticizer.

The reaction vessel can be as conventional as laboratory glassware such as a beaker with a magnetic stirrer on a mixing hotplate to as specialized as a three-necked round-bottom flask with a mechanical stirrer on a heating mantle or commercially scaled equivalents thereof. Scale-up from lab bench reaction to commercial production is a process not unfamiliar to those of ordinary skill in the art without undue experimentation being required. Scale-up can move from batch processing to continuous processing.

USEFULNESS OF THE INVENTION

The usefulness of unhindered polyols, preferably using the combination of catalysts, is apparent from the ability to produce epoxidized soyate diesters with intact epoxy groups and a yield of diesters as high as 80% with a residual epoxidized soyate content of under 5%. This achievement is truly unexpected in the art because (a) epoxy groups are unlikely to survive transesterification reactions under forcing conditions which typically uses strong bases to achieve a high conversion rate, thereby attacking the epoxy group and (b) transesterification from a mono-soyate to a disoyate is unlikely to yield over 50% of disoyate because transesterification is an equilibrium reaction between reactants, the mono-soyate, and the disoyate, especially at the molar ratios identified in Table 1 above. The reaction equilibrium is pushed forward toward the desired product by removal of the alcohol present. Neither catalyst alone can achieve such results, as the Examples below report.

Usefulness of an epoxidized soyate diester with intact epoxy groups is first and foremost as a bioderived plasticizer for any rigid thermoplastic or thermoset matrix which needs to be made more flexible. Any conventional use of any phthalate plasticizer today is a candidate use for epoxidized soyate diesters made using the method of the present invention, relying on the combination of catalysts of the present invention. Polyvinyl halide, particularly polyvinyl chloride (PVC), constitutes a substantial use of plasticizers to make flexible PVC compounds and PVC plastisols from starting from PVC resins.

The amount of plasticizer in a flexible solid compound can range from about 10 to about 60, and preferably from about 30 to about 50 weight percent of the total compound, with the remainder being a thermoplastic (such as PVC) or thermoset polymer.

The amount of plasticizer in a plastisol can range from about 10 to about 90, and preferably from about 60 to about 85 weight percent of the total compound, with the remainder being thermoplastic polymer such as PVC.

Presently preferred as a bioderived plasticizer is epoxidized 1,3-propanediol disoyate arising from the reaction according to the present invention of epoxidized methyl soyate and 1,3-propanediol.

Polyvinyl Chloride Resins

Polyvinyl chloride polymers are widely available throughout the world. Polyvinyl chloride resin as referred to in this specification includes polyvinyl chloride homopolymers, vinyl chloride copolymers, graft copolymers, and vinyl chloride polymers polymerized in the presence of any other polymer such as a HDT distortion temperature enhancing polymer, impact toughener, barrier polymer, chain transfer agent, stabilizer, plasticizer or flow modifier.

For example a combination of modifications may be made with the PVC polymer by overpolymerizing a low viscosity, high glass transition temperature (Tg) enhancing agent such as SAN resin, or an imidized polymethacrylate in the presence of a chain transfer agent.

In another alternative, vinyl chloride may be polymerized in the presence of said Tg enhancing agent, the agent having been formed prior to or during the vinyl chloride polymerization. However, only those resins possessing the specified average particle size and degree of friability exhibit the advantages applicable to the practice of the present invention.

In the practice of the invention, there may be used polyvinyl chloride homopolymers or copolymers of polyvinyl chloride comprising one or more comonomers copolymerizable therewith. Suitable comonomers for vinyl chloride include acrylic and methacrylic acids; esters of acrylic and methacrylic acid, wherein the ester portion has from 1 to 12 carbon atoms, for example methyl, ethyl, butyl and ethylhexyl acrylates and the like; methyl, ethyl and butyl methacrylates and the like; hydroxyalkyl esters of acrylic and methacrylic acid, for example hydroxymethyl acrylate, hydroxyethyl acrylate, hydroxyethyl methacrylate and the like; glycidyl esters of acrylic and methacrylic acid, for example glycidyl acrylate, glycidyl methacrylate and the like; alpha, beta unsaturated dicarboxylic acids and their anhydrides, for example maleic acid, fumaric acid, itaconic acid and acid anhydrides of these, and the like; acrylamide and methacrylamide; acrylonitrile and methacrylonitrile; maleimides, for example, N-cyclohexyl maleimide; olefin, for example ethylene, propylene, isobutylene, hexene, and the like; vinylidene halide, for example, vinylidene chloride; vinyl ester, for example vinyl acetate; vinyl ether, for example methyl vinyl ether, allyl glycidyl ether, n-butyl vinyl ether and the like; crosslinking monomers, for example diallyl phthalate, ethylene glycol dimethacrylate, methylene bis-acrylamide, tracrylyl triazine, divinyl ether, allyl silanes and the like; and including mixtures of any of the above comonomers.

The preferred composition is a polyvinyl chloride homopolymer.

Commercially available sources of polyvinyl chloride polymers include Oxyvinyls LP of Dallas, Tex. and Shin Tech USA of Freeport, Tex.

Flexible PVC Compounds

Flexible PVC resin compounds (fPVC) contain PVC resin and plasticizer. Due the considerable variety of uses of flexible PVC compounds, a variety of additives can be selected according to the performance requirements of the article produced therefrom well within the understanding of one skilled in the art without the necessity of undue experimentation.

Optional PVC Compound Ingredients

The PVC compounds used herein optionally contain effective amounts of additives ranging from 0 to about 500 weight parts per 100 weight parts PVC (parts per hundred resin—phr).

For example, various primary and/or secondary lubricants such as oxidized polyethylene, paraffin wax, fatty acids, and fatty esters and the like can be utilized.

Thermal and ultra-violet light (UV) stabilizers can be utilized such as various organo tins, for example dibutyl tin, dibutyltin-S—S'-bi-(isooctylmercaptoacetate), dibutyl tin dilaurate, dimethyl tin diisooctylthioglycolate, mixed metal stabilizers like Barium Zinc and Calcium Zinc, and lead stabilizers (tri-basic lead sulfate, di-basic lead phthalate, for example). Secondary stabilizers may be included for example a metal salt of phosphoric acid, polyols, and epoxidized oils. Specific examples of salts include water-soluble, alkali metal phosphate salts, disodium hydrogen phosphate, orthophosphates such as mono-, di-, and tri-orthophosphates of said alkali metals, alkali metal polyphosphates, -tetrapolyphosphates and -metaphosphates and the like. Polyols such as sugar alcohols, and epoxides such as epoxidized soybean oil can be used. Typical levels of secondary stabilizers range from about 0.1 wt. parts to about 10.0 wt. parts per 100 wt. parts PVC (phr).

In addition, antioxidants such as phenolics, BPA, BHT, BHA, various hindered phenols and various inhibitors like substituted benzophenones can be utilized.

When increased impact values are desired, impact modifiers can be included which are known to the art. For example, various impact modifiers are set forth in The Encyclopedia of PVC, Volume 2, Chapter 12, Marcel Dekker, Inc., New York, 1977. Specific examples of impact modifiers include various acrylonitrile-butadiene-styrene (ABS) polymers, the various chlorinated polyethylenes, the various graft copolymers of acrylic rubbers, the various poly(ethylene-co-vinyl acetates), graft copolymers of methylmethacrylate, butadiene and styrene (MBS), graft copolymers of acrylonitrile, butadiene and styrene (ABS) and the like. Impact modifiers of these types are commercially available. Preferred impact modifiers include ABS, MBS, graft copolymers of acrylic rubbers, chlorinated polyethylene and mixtures. Regardless of the particular impact modifier utilized, the amounts thereof can naturally vary, depending upon the desired impact strength as typically measured by an Izod impact test (ASTM D256). The levels of impact modifier present typically vary from about 3 to about 30 phr. Accordingly, articles derived from the powder compounds of the present invention have the capacity to be impact-modified to achieve notched Izod values generally in excess of in excess of 100 N/m2 if desired.

Various processing aids, fillers, pigments, flame retardants and reinforcing materials can also be utilized in amounts up to about 200 or 300 phr. Exemplary processing aids are acrylic polymers such as poly methyl (meth)acrylate based materials.

Adjustment of melt viscosity can be achieved as well as increasing melt strength by employing 0.5 to 5 phr of commercial acrylic process aids such as those from Rohm and Haas under the Paraloid® trademark. Paraloid®. K-120ND, K-120N, K-175, and other processing aids are disclosed in The Plastics and Rubber Institute: International Conference on PVC Processing, Apr. 26-28 (1983), Paper No. 17.

Examples of fillers include calcium carbonate, clay, silica and various silicates, talc, carbon black and the like. Reinforcing materials include glass fibers, polymer fibers and cellulose fibers. Such fillers are generally added in amounts of from about 3 to about 500 phr of PVC. Preferably from 3 to 300 phr of filler are employed for extruded profiles such as louvers or cove base moldings. Also, flame retardant fillers like ATH (Aluminum trihydrates), AOM (ammonium octamolybdate), antimony trioxides, magnesium oxides and zinc borates are added to boost the flame retardancy of polyvinyl chloride. The concentrations of these fillers range from 1 phr to 200 phr.

Examples of various pigments include titanium dioxide, carbon black and the like. Mixtures of fillers, pigments and/or reinforcing materials also can be used.

The compound of the present invention can include other conventional plastics additives in an amount that is sufficient to obtain a desired processing or performance property for the compound. The amount should not be wasteful of the additive nor detrimental to the processing or performance of the compound. Those skilled in the art of thermoplastics compounding, without undue experimentation but with reference to such treatises as *Plastics Additives Database* (2004) from Plastics Design Library (www.williamandrew.com), can select from many different types of additives for inclusion into the compounds of the present invention.

Non-limiting examples of other optional additives include adhesion promoters; biocides (antibacterials, fungicides, and mildewcides), anti-fogging agents; anti-static agents; bonding, blowing and foaming agents; dispersants; fillers and extenders; fire and flame retardants and smoke suppresants; impact modifiers; initiators; lubricants; micas; pigments, colorants and dyes; plasticizers; processing aids; release agents; silanes, titanates and zirconates; slip and anti-blocking agents; stabilizers; stearates; ultraviolet light absorbers; viscosity regulators; waxes; and combinations of them.

Processing

The preparation of PVC compounds of the present invention is uncomplicated. The compound can be made in batch or continuous operations from a powder blend which is typically prepared in a batch-wise operation.

Such powder blending in a batch process typically occurs in a powder mixer such as a Henschel or Littleford mixer, or a ribbon blender that physically mixes all the additives including plasticizers with PVC resin without bringing the polymer matrix to a melting temperature. The mixing speeds range from 60 to 3000 rpm and temperature of mixing can be ambient up to 250 F. The output from the mixer is a well blended powder product that can flow into a machine that can bring up the blend temperature to induce melting of some ingredients including the PVC resin.

Mixing in a batch process typically occurs in a Banbury mixer that is also elevated to a temperature that is sufficient to melt the polymer matrix to permit addition of the solid ingredient additives of any optional additive. The mixing speeds range from 60 to 3000 rpm and temperature of mixing ranges from 120° C. to 220° C. (250° F. to 430° F.). Also, the output from the mixer is chopped into smaller sizes for later extrusion or molding into polymeric articles.

Compounds can be formed into powder, cubes, or pellets for further extrusion or molding into polymeric components and parts.

Subsequent extrusion or molding techniques are well known to those skilled in the art of thermoplastics polymer engineering. Without undue experimentation but with such references as "Extrusion, The Definitive Processing Guide and Handbook"; "Handbook of Molded Part Shrinkage and Warpage"; "Specialized Molding Techniques"; "Rotational Molding Technology"; and "Handbook of Mold, Tool and Die Repair Welding", all published by Plastics Design Library (www.williamandrew.com), one can make articles of any conceivable shape and appearance using compounds of the present invention.

PolyOne Corporation (www.polyone.com) is a worldwide maker and seller of plasticized polyvinyl chloride compounds used as packaging, industrial parts, consumer goods, and other purposes.

Vinyl Plastisols

Vinyl plastisols are typically liquid at room temperature and can be poured, pumped, sprayed or cast, depending on the compound. These compounds can range in hardness from fishing lure plastisol with an 8 Durometer Shore A, to rotocasting plastisol with a 65 Durometer Shore D. Advantages of vinyl plastisol in coating and molding applications include ease of use and economy. Plastisols can be formed from dispersion-grade poly(vinyl chloride) (PVC) resins (homopolymers and copolymers) and plasticizers. Exemplary dispersion-grade PVC resins are disclosed in U.S. Pat. Nos. 4,581,413; 4,693,800; 4,939,212; and 5,290,890, incorporated by reference herein, among many others such as those referenced in the above four patents.

Optional Plastisol Ingredients

A variety of ingredients commonly used in the coatings industry can also be included in the mixture. Non-limiting examples of such optional additives include slip agents, antiblocking agents, antioxidants, ultraviolet light stabilizers, quenchers, plasticizers, mold release agents, lubricants, antistatic agents, fire retardants, and fillers such as glass fibers, talc, chalk, or clay. Of these fillers, the properties of nanoclay can add stiffness, toughness, and charring properties for flame retardancy. Such optional additives can be included in the mixture in an amount from about 0 to about 95, and preferably from about 0.1 to about 50 weight percent. Most preferably, the amount is about 1 to about 40 weight percent of the mixture.

Any conventional colorant useful in coatings and paints is also acceptable for use in these plastisols. Conventional colorants can be employed, including inorganic pigments such as titanium dioxide, iron oxide, chromium oxide, lead chromate, carbon black, silica, talc, china clay, metallic oxides, silicates, chromates, etc., and organic pigments, such as phthalocyanine blue, phthalocyanine green, carbazole violet, anthrapyrimidine yellow, flavanthrone yellow, isoindoline yellow, indanthrone blue, quinacridone violet, perylene reds, diazo red and others. The amount of colorant can range from none at all to about 40, and preferably from about 1.5 to about 20 weight percent of the mixture.

Processing

The making of plastisols is straightforward to those of ordinary skill in the art. One can make in batch or continuous operations from a powder blend of dispersion grade PVC resin, plasticizer, and optional other ingredients.

Such powder blending in a batch process typically occurs in a powder mixer such as a Henschel or Littleford mixer, or a ribbon blender that physically mixes all the additives including plasticizers with PVC resin without bringing the polymer matrix to a melting temperature. The mixing speeds range from 60 to 3000 rpm and temperature of mixing can be ambient up to 250 F. The output from the mixer is a well blended powder product that can flow and remain liquid after cooling because of the volume of plasticizer present.

The plastisol is then ready for use in dip coating, hot dipping, cold dipping, slush molding, rotational molding, dip molding, open molding, knife coating, roll coating, reverse roll coating, screen printing, and other mechanical techniques known to those skilled in the art to convert a plastisol to a final article.

PolyOne Corporation is also a worldwide maker and seller of plastisols used as coatings, inks, and other purposes.

EXAMPLES

Comparative Example A and Examples 1-6

Table 2 shows the ingredients and their sources. Table 3 shows the recipes, preparation, and resulting properties.

Size exclusion chromatography (SEC) was used to determine the amounts of residual epoxidized methyl soyate, the yield of monoester, and the yield of diester. Carbon nuclear magnetic resonance (13C-NMR) spectroscopy was used to determine the intact nature of the epoxy groups after reaction.

TABLE 2

Ingredients

| Ingredient Name | Commercial Source | Other Info. |
|---|---|---|
| Epoxidized Methyl Soyate ("Lab EMS") Soyate Reactant | Lab-made according to the process described above in Paragraph [00025] | |
| Epoxidized Methyl Soyate ("Vikoflex EMS") Soyate Reactant | Vikoflex ® 7010 from Arkema of Philadelphia, PA | CAS# 68082-35-9; LOT# ASCAP101V |
| 1,2-propanediol ("1,2-diol") | Sigma-Aldrich | CAS# 57-55-6 |
| 1,3-propanediol ("1,3-diol") Polyol Reactant | Fluka ® 1,3-diol from Aldrich of Milwaukee, WI | CAS# 504-63-2; ≧99% (GC) |
| Potassium hydroxide (KOH) Primary Catalyst | Aldrich | Flakes needing MeOH |
| Tetrakis(2-ethylhexyl) orthotitanate ("Titanate") Secondary Catalyst | TYZOR ® TOT from DuPont of Wilmington, DE | CAS# 1070-10-6; LOT# 304; 95%~99% |
| Methanol ("MeOH") solvent for KOH | Fisher Scientific of Pittsburgh, PA | CAS# 67-56-1; LOT# 072825; 99.9% |
| 1,4-butanediol ("1,4-diol") | Sigma-Aldrich | CAS# 110-63-4 |
| 1,6-hexanediol ("1,6-diol") | Sigma-Aldrich | CAS# 629-11-8 |

TABLE 3

Recipes, Preparation, and Properties

| Ingredient Name (Amounts in moles) | Comp. Example A | Example 1 | Example 2 | Example 3 | Example 4 | Example 5 | Example 6 |
|---|---|---|---|---|---|---|---|
| Lab EMS | 1.0 | 1.0 | 1.0 | 1.0 | | 1.0 | 1.0 |
| Vikoflex ® 7010 EMS | | | | | 1.0 | | |
| 1,2-diol | 0.3749 | | | | | | |
| 1,3-diol | | 0.4218 | 0.4219 | 0.4304 | 0.4270 | | |
| 1,4-diol | | | | | | 0.4310 | |
| 1,6-diol | | | | | | | 0.4264 |
| KOH | 0.02825 | 0.01693 | 0.0185 | 0.0195 | 0.0211 | 0.03295 | 0.03392 |
| Titanate | | | 0.0073 | 0.0091 | 0.0149 | 0.0146 | 0.01472 |
| MeOH | 0.2908 | 0.1743 | 0.1906 | 0.2010 | 0.2173 | 0.3392 | 0.3491 |
| Mixing Equipment | Magnetically stirred on a 25 ml round-bottom flask on a Corning Stirrer/Hot Plate | | | | | | |
| Mixing Temp. | 50° C. | 65° C. | 65° C. | 75° C. | 65° C. | 65° C. | 65° C. |
| Mixing Duration | 16 hours | 16 hours | | | 20 hours | | |
| Mixing Speed | Setting the Corning Stirrer/Hot Plate (6" × 5") at "8" (stirring vigorously) | | | | | | |
| $N_2$ Protection | No | | | Yes | | | |
| Order of Addition of Ingredients | EMS + diol, then KOH/MeOH | | EMS + diol, then KOH/MeOH, lastly adding Titanate after stirring 30 min under $N_2$. | | | | |
| Form of Product After Mixing | Viscous liquid | Low viscous liquid | Very viscous liquid, becomes solid after sitting overnight | | | Slightly viscous liquid | Viscous liquid |
| Residual EMS, % | 57.0 | 32.5 | 14.5 | 4.1 | 19.1 | 55 | 33.8 |
| Epoxidized Monoester Yield (%) | 27.8 | 22.1 | 6.6 | 2.3 | 16.4 | 29.2 | 26.3 |
| Epoxidized Diester Yield (%) | 11.0 | 41.7 | 72.3 | 80.8 | 58.6 | 13.0 | 35.0 |
| Intact Epoxy Groups | Yes, with observation of 13C-NMR graphs showing nearly all starting epoxy groups are retained. | | | | | Not tested | |

Comparative Example A showed that the hindered 1,2-propanediol using KOH as a primary catalyst only yielded about 11% of the desired epoxidized diester.

Example 1 showed that the same reaction conditions, but with unhindered 1,3-propanediol nearly quadrupled (41%) the yield of the desired epoxidized diester.

Therefore, all other factors being constant, the presence of hydroxyl functionality on adjacent carbon atoms of the diol limited the desired diester yield, believed to be due to undesired steric hindrance effects.

Examples 2-4 introduce the preferred combination of catalysts of KOH and titanate for use with unhindered 1,3-propanediol. The ratio of Diester to Monoester yield was excellent for Example 2 and unexpectedly spectacular for Example 3. The miniscule residual epoxidized soyate of Example 3 combined with the diester yield of 80% was totally unexpected. The reaction at 75° C. contributed to this result.

While the results for Examples 5 and 6 do not yet achieve the same yields as those seen for Examples 1-4, further refinement using processing techniques known to those skilled in the art, without undue experimentation, will result in a variety of epoxidized soyate diesters with differing polyol segments.

The invention is not limited to the above embodiments. The claims follow.

What is claimed is:

1. A method of making an epoxidized soyate diester, comprising the step of mixing under heat and agitation
    (a) epoxidized soyate;
    (b) unhindered polyol; and
    (c) a catalyst
to make an epoxidized soyate diester.

2. The method of claim 1, wherein the unhindered polyol is selected from the group consisting of 1,3-propanediol, 2-methyl-1,3-propanediol, 2,2'-dimethyl-1,3-propanediol, 1,3-butanediol, 1,4-butanediol, 2-methyl-1,4-butanediol, 1,5-pentanediol, 2-methyl-2,4-pentanediol, 3-methyl-1,5-pentanediol, 1,3-hexanediol, 1-4-hexanediol, 1,5-hexanediol, 1,6-hexanediol, 2,2'-dihydroxypropyl ether, diethylene glycol, dipropylene glycol, triethylene glycol, and combinations thereof.

3. The method of claim 1, wherein the catalyst is a catalyst system, comprising:
    (a) a primary catalyst comprising a metallic hydroxide and
    (b) a secondary catalyst comprising a titanate.

4. The method of claim 3, wherein the primary catalyst is a metallic hydroxide flake dissolved in alcohol for further processing.

5. The method of claim 3, wherein the metallic hydroxide is an alkali metal hydroxide or an alkaline metal earth hydroxide.

6. The method of claim 5, wherein the metallic hydroxide is potassium hydroxide.

7. The method of claim 5, wherein the secondary catalyst is selected from the group consisting of 2-ethylhexyl titanate, tetraisopropyl titanate, tetrabutyl titanate, tetrakis-2-ethylhexyl titanate, and combinations thereof.

8. The method of claim 7, wherein the secondary catalyst is tetrakis-2-ethylhexyl titanate.

9. The method of claim 3, wherein the epoxidized soyate monoester is selected from the group consisting of epoxidized methyl soyate, epoxidized ethyl soyate, epoxidized butyl soyate, epoxidized octyl soyate, and combinations thereof.

10. The method of claim 9, wherein the epoxidized soyate monoester has from about 0.5 to about 4 epoxy groups per molecule.

11. The method of claim 9, wherein the epoxidized soyate is epoxidized methyl soyate and the polyol is 1,3-propanediol and wherein the resulting product of reaction is epoxidized 1,3-propanediol disoyate.

12. The method of claim 3, wherein the molar ratio of the polyol, the metallic hydroxide, the titanate, and the optional alcohol solvent relative to the epoxidized soyate ranges according to the following table:

| | |
|---|---|
| Epoxidized soyate | 1.0 |
| Unhindered Polyol | 0.2-0.5 |
| Metallic hydroxide | 0.01-0.02 |
| Titanate | 0.007-0.015 |
| Optional alcohol solvent | 0-0.22 |

13. An epoxidized soyate diester selected from the group consisting of epoxidized 1,3-propanediol disoyate, epoxidized 2-methyl-1,3-propanediol disoyate, epoxidized 2,2'-dimethyl-1,3-propanediol disoyate, epoxidized 1,3-butanediol disoyate, epoxidized 1,4-butanediol disoyate, epoxidized 2-methyl-1,4-butanediol disoyate, epoxidized 1,5-pentanediol disoyate, epoxidized 2-methyl-2,4-pentanediol disoyate, epoxidized 3-methyl-1,5-pentanediol disoyate, epoxidized 1,3-hexanediol disoyate, epoxidized 1-4-hexanediol disoyate, epoxidized 1,5-hexanediol disoyate, epoxidized 1,6-hexanediol disoyate, epoxidized 2,2'-dihydroxypropyl ether disoyate, epoxidized diethylene glycol disoyate, epoxidized dipropylene glycol disoyate, epoxidized triethylene glycol disoyate, and combinations thereof.

14. A method of using the epoxidized soyate diester of claim 13, comprising the step of mixing the diester with a thermoplastic or thermoset polymer to form a plasticized polymer compound.

15. The method of claim 14, wherein the polymer is polyvinyl chloride in the form of a flexible solid.

16. The method of claim 14, wherein the polymer is polyvinyl chloride in the form of a plastisol.

17. A flexible polymer compound, comprising:
 (a) 40-90 weight percent of polymer and
 (b) 10-60 weight percent an epoxidized soyate diester of claim 13.

18. A plastisol, comprising:
 (a) 10-90 weight percent of thermoplastic polymer and
 (b) 10-90 weight percent of an epoxidized soyate diester of claim 13.

* * * * *